United States Patent [19]

Holtkamp

[11] Plant 4,214

[45] Feb. 14, 1978

[54] AFRICAN VIOLET PLANT

[76] Inventor: Reinhold Holtkamp, Weatherstrasse 112, 4294 Isselburg, Germany

[21] Appl. No.: 774,047

[22] Filed: Mar. 3, 1977

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

A novel African violet characterized by its large, pink blossoms borne on strong stems and over a long period of time.

2 Drawing Figures

1

The present invention comprises a new and distinct cultivar of African violet plant, botanically known as *Saintpaulia ionantha,* and hereinafter referred to by the cultivar name New Jersey. The new cultivar, which was designated during the breeding and selection process by No. b17/2 - 44/76, is the product of a planned breeding program. The unpatented female parent, F III pink frilled, color 43-1, was selected for breeding because of the frilled edges of the flower petals and pink flower color. The unpatented male or pollen parent, XIX 4001, red color, was selected for breeding due to its upright and strong flower stems and attractive shiny leaves surrounding the flower bouquet. The male parent is also characterized by its excellent red flower color.

The new cultivar was originated from a cross made in a controlled breeding program in Isselburg, Rhineland, Germany, and was discovered and selected as a flowering plant within the progeny of the stated cross by me in a controlled environment at the same location. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of the new cultivar New Jersey, which in combination distinguish this African violet as a new and distinct cultivar:

1. Large flowers which do not drop.
2. Upright and strong flower stems which form a flower bouquet above the leaves.
3. Attractive pink frilled flowers having long blooming period.
4. Attractive saleable plant with the first flash of flowers.

The accompanying photographic drawings show a typical specimen plant of the new cultivar, with the colors appearing in the photographs being as true as possible with color illustrations of this type.

FIG. 1 is a view of the entire plant in bloom, and

FIG. 2 shows the buds and the top and underside of the flower petals and leaves at various stages of growth.

In the following description, color references are made to the Munsell Color Cascade chart, except where general color terms are employed.

2

Botanical classification: *Saintpaulia ionantha,* Ramat. cv. New Jersey

Parentage:

*Male parent.*—XIX 4001 red.

*Female parent.*—f III pink frilled, color 43-1.

Propagation: The new cultivar holds its distinguishing characteristics through successive propagations by leaf cuttings and by division of shoots.

Plant: From 8 cm. to 10 cm. tall when grown in pots, and approximately 25 cm. in diameter when fully grown.

Leaves:

*General form.*—Round to oval.

*Diameter.*—When mature, 60–65 mm.

*Texture.*—Soft and hairy.

*Aspect.*—Velvety.

*Veins.*—Underside, well pronounced, reddish.

*Color (upperside).*—22-16.

*Color (underside).*—Light green, with generally brown-red venation in early stages.

*Petiole.*—Brownish-red.

Flowers:

*Buds.*—Ballshaped, 2 mm. when small, 6–10 mm. before opening, color 39-1.

*Sepals.*—Five, two small, three large, all frilled. Color: Green-brown on the tip, turning to brown. Calyx: Funnel-shaped. Aspect: Spear-shaped, hairy. Peduncle: Brownish-red.

Individual flowers:

*Size.*—45–50 mm., almost flat.

*Color.*—(Upperside): 42-4. (Underside): 42-3.

*Borne.*—5–8 flowers on strong stems and peduncles.

*Shape.*—Five petals, 2 small and 3 large, with frilled edge; a few flowers have a small petal more in the center.

*Corolla.*—The large petals measured from the center are 22–25 mm. long and 25 mm. wide.

*Arrangement.*—Strong and upright peduncles with up to 8 flowers on young plant with the first flower.

*Flowering time.*—Approximately 6–8 weeks after potting the first flowers appear, and 2 weeks later the plant is saleable with a nice flower head.

Reproductive organs:

*Anthers.*—Two, 3–4 mm. wide, color 28-4 golden yellow; capsule pushes slightly through.

*Arrangement.*—Basifixed.

*Filaments.*—4–5 mm., base light green, middle part on outside light reddish; connection to anthers light green.

*Styles.*—Base light green, anther part to the tip, color 43-5.

*Pollen color.*—Light yellow 27-2.

Roots: Well developed root system.

Disease resistance: Very good to date.

General observations: New Jersey is a unique cultivar. The flowers are carried on strong, upright stems and the flowers do not drop after maturity. After the first flowers are removed, a second full flowering takes place in approximately 6–8 weeks, and the plant shows a flower head nearly double in diameter to the first. On second flowering, the pink flower color and the flower size makes the plant even more attractive than when first in flower.

I claim:

1. A new and distinct cultivar of African violet plant known by the cultivar name New Jersey and particularly characterized as to uniqueness by the combined characteristics of large pink flowers with frilled edges, with the flowers being non-dropping; long blooming period; upright and strong flower stems which form a bouquet above the leaves; and by the characteristic of being a saleable plant with the first flash of flowers.

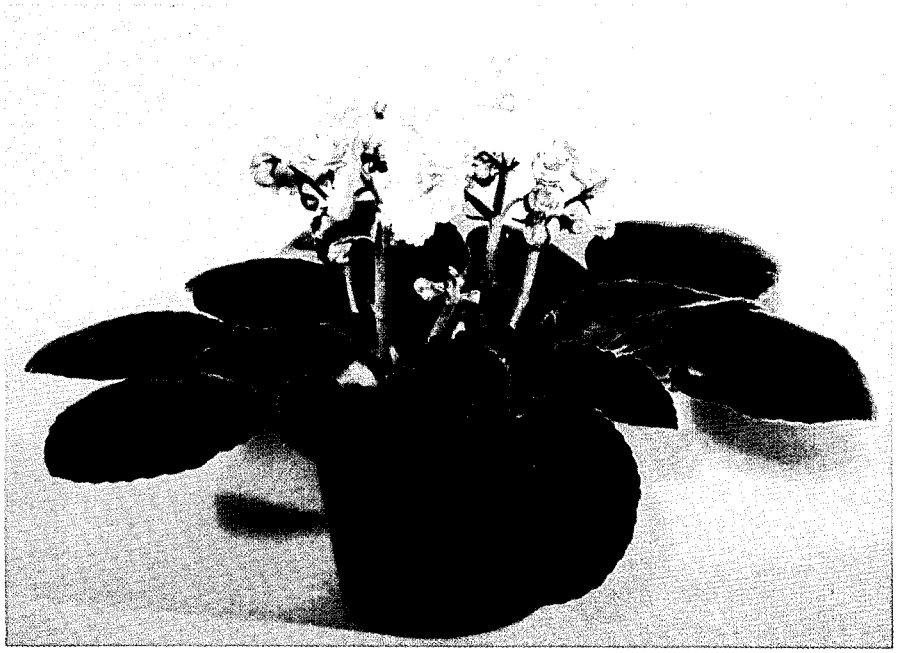

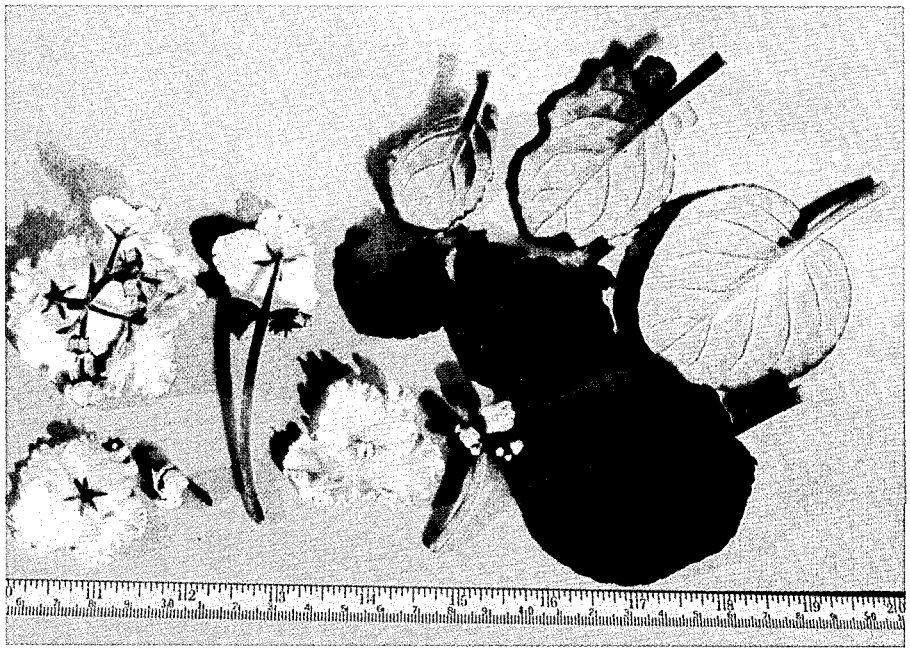

* * * * *